United States Patent
Kitamura

(10) Patent No.: US 8,262,954 B2
(45) Date of Patent: Sep. 11, 2012

(54) METHOD OF PRODUCING GRANULAR SUBSTANCE

(75) Inventor: Kazuhiro Kitamura, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 183 days.

(21) Appl. No.: 12/790,142

(22) Filed: May 28, 2010

(65) Prior Publication Data

US 2010/0314787 A1    Dec. 16, 2010

(30) Foreign Application Priority Data

Jun. 12, 2009  (JP) ................. 2009-141146

(51) Int. Cl.
  *B29B 9/00* (2006.01)
  *C07C 69/52* (2006.01)
(52) U.S. Cl. ............... 264/13; 560/138; 560/140
(58) Field of Classification Search .......... None
  See application file for complete search history.

(56) References Cited

U.S. PATENT DOCUMENTS

| | | | | |
|---|---|---|---|---|
| 1,637,377 A * | 8/1927 | Heicke | | 425/10 |
| 2,570,423 A * | 10/1951 | Batchelder et al. | | 425/10 |
| 4,525,514 A * | 6/1985 | Yachigo et al. | | 524/291 |
| 4,824,616 A * | 4/1989 | Shimizu et al. | | 264/7 |
| 5,214,193 A * | 5/1993 | Inoue et al. | | 560/140 |
| 5,616,780 A | 4/1997 | Pitteloud et al. | | |
| 7,413,690 B1 * | 8/2008 | Cheboyina et al. | | 264/13 |
| 7,968,020 B2 * | 6/2011 | Behelfer et al. | | 264/11 |
| 7,977,418 B2 * | 7/2011 | Kimura et al. | | 524/291 |
| 2009/0197997 A1 * | 8/2009 | Kitamura et al. | | 524/115 |
| 2010/0056680 A1 * | 3/2010 | Kimura et al. | | 524/291 |

FOREIGN PATENT DOCUMENTS

| | | |
|---|---|---|
| EP | 0265792 A1 | 5/1988 |
| EP | 0322166 A1 | 6/1989 |
| EP | 0 421 932 A1 | 4/1991 |
| EP | 0 719 824 A2 | 7/1996 |
| EP | 0 905 180 A2 | 3/1999 |
| EP | 2 017 299 A1 | 1/2009 |
| EP | 2 159 214 A2 | 3/2010 |
| EP | 2 172 512 A1 | 4/2010 |

OTHER PUBLICATIONS

European Search Report dated Aug. 18, 2010 for Application No. 10165536.3.
Hungarian Examination Report dated Jul. 15, 2011, for Application No. 201003647-3.

* cited by examiner

*Primary Examiner* — Mary F Theisen
(74) *Attorney, Agent, or Firm* — Birch, Stewart, Kolasch & Birch, LLP

(57) ABSTRACT

A method of producing a granular substance comprising
  (i) a step of melting a compound of the formula (1):

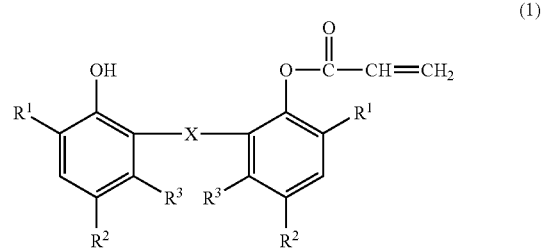

(wherein, $R^1$ and $R^2$ represent each independently a hydrogen atom, alkyl group having 1 to 8 carbon atoms or cycloalkyl group having 5 to 8 carbon atoms, $R^3$ represents a hydrogen atom or alkyl group having 1 to 8 carbon atoms. X represents a single bond, sulfur atom, oxygen atom, alkylidene group having 1 to 8 carbon atoms or cycloalkylidene group having 5 to 8 carbon atoms) to obtain the melted substance, and
  (ii) a step of dropping the melted substance obtained in the step (i) into water and recovering the granular substance.

5 Claims, No Drawings

METHOD OF PRODUCING GRANULAR SUBSTANCE

TECHNICAL FIELD

The present invention relates to a method of producing a granular substance.

BACKGROUND ART

It is known to blend a compound of the formula (1-1) into a polymer, for improving the processing stability of the polymer such as polybutadiene and the like (see, e.g., patent documents 1 and 2).

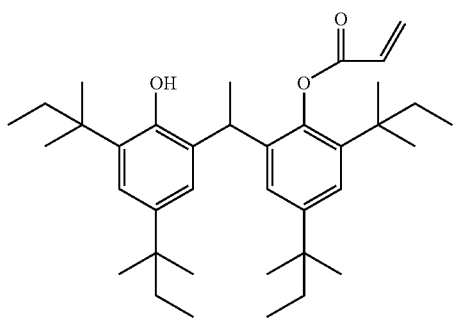

(1-1)

(Patent document 1) JP-A No. 1-168643 (Production Example 1)
(Patent document 2) JP-A No. 4-264051 (Example 1)

SUMMARY OF THE INVENTION

The compound of the above-described formula (I-1) is obtained as a crystal in the form of powder, thus, there is a problem of generation of dusting, for example, in an operation of blending the compound into a polymer.

For solving such a problem, the present inventors have investigated, leading resultantly to completion of the present invention.

That is, the present invention provides the following [1] to [7].

[1]. A method of producing a granular substance comprising
(i) a step of melting a compound of the formula (I):

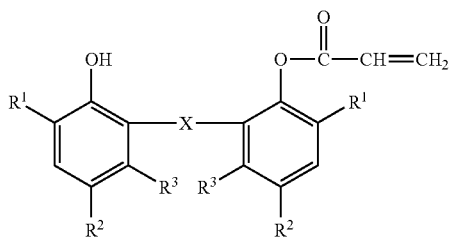

(1)

(wherein, $R^1$ and $R^2$ represent each independently a hydrogen atom, alkyl group having 1 to 8 carbon atoms or cycloalkyl group having 5 to 8 carbon atoms, $R^3$ represents a hydrogen atom or alkyl group having 1 to 8 carbon atoms. X represents a single bond, sulfur atom, oxygen atom, alkylidene group having 1 to 8 carbon atoms or cycloalkylidene group having 5 to 8 carbon atoms) to obtain the melted substance, and
(ii) a step of spraying or dropping the melted substance obtained in the step (i) into water and recovering the granular substance.

[2]. The production method according to [1], wherein the melted substance obtained in the step (i) is dropped into water containing surfactant.

[3]. The production method according to [2], wherein the surfactant is a surfactant having an HLB value of 2 to 6.

[4]. The production method according to any one of [1] to [3], wherein the melted substance obtained in the step (i) is dropped into water having a temperature which is not lower than 20° C. and lower than the melting point of the compound of the formula (I).

[5]. The production method according to any one of [1] to [4], wherein the weight of per grain of the resultant granular substance is 5 mg to 100 mg.

[6]. The production method according to any one of [1] to [5], wherein the compound of the formula (1) is 2-[1-(2-hydroxy-3,5-di-t-pentylphenyl)ethyl]-4,6-di-t-pentylphenyl acrylate or 2-t-butyl-6-(3-t-butyl-2-hydroxy-5-methylbenzyl)-4-methylphenyl acrylate.

[7]. The production method according to any one of [1] to [6], wherein the resultant granular substance has a shape of disc, approximate sphere or approximate hemisphere.

MODES FOR CARRYING OUT THE INVENTION

The granular substance obtained by the production method of the present invention contains a compound of the formula (1) (hereinafter, referred to as compound (1) in some cases).

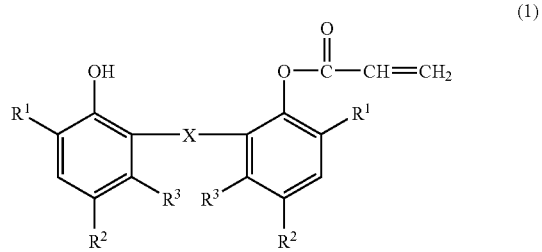

(1)

In the formula (1), $R^1$ and $R^2$ represent each independently a hydrogen atom, alkyl group having 1 to 8 carbon atoms or cycloalkyl group having 5 to 8 carbon atoms. Here, exemplified as the alkyl group having 1 to 8 carbon atoms are a methyl group, ethyl group, n-propyl group, i-propyl group, n-butyl group, i-butyl group, t-butyl group, n-pentyl group, i-pentyl group, t-pentyl group, 2-ethylhexyl group and the like, and exemplified as the cycloalkyl group having 5 to 8 carbon atoms are a cyclopentyl group, cyclohexyl group, cyclooctyl group, 3-methylcyclopentyl, 4-methylcyclopentyl group, 3-methylcyclohexyl group and the like.

$R^3$ represents a hydrogen atom or alkyl group having 1 to 8 carbon atoms. As the alkyl group $R^3$, alkyl groups as exemplified for $R^1$ and the like are specifically exemplified.

X represents a single bond, sulfur atom, oxygen atom, alkylidene group having 1 to 8 carbon atoms or cycloalkylidene group having 5 to 8 carbon atoms.

Here, exemplified as the alkylidene group having 1 to 8 carbon atoms are a methylene group, ethylidene group, propylidene group, butylidene group and the like, and exemplified as the cycloalkylidene group having 5 to 8 carbon atoms are a cyclopentylidene group, cyclohexylidene group and the like.

The melting point of the compound (1) is usually 70 to 220° C., preferably 100 to 140° C.

As the compound (1), for example, 2-[1-(2-hydroxy-3,5-di-t-pentylphenyl)ethyl]-4,6-di-t-pentylphenyl acrylate, 2-[1-(2-hydroxy-3,5-di-t-pentylphenyl)ethyl]-4,6-di-t-pentylphenyl methacrylate, 2-(2-hydroxy-3,5-di-t-pentylbenzyl)-4,6-di-t-pentylphenyl acrylate, 2,4-di-t-butyl-6-[1-(3,5-di-t-butyl-2-hydroxyphenyl)ethyl]phenyl acrylate, 2,4-di-t-butyl-6-(3,5-di-t-butyl-2-hydroxybenzyl)phenyl acrylate, 2,4-di-t-butyl-6-[1-(3,5-di-t-butyl-2-hydroxyphenyl)ethyl]phenyl methacrylate, 2-t-butyl-6-(3-t-butyl-2-hydroxy-5-methylbenzyl)-4-methylphenyl acrylate, 2-t-butyl-6-[1-(3-t-butyl-2-hydroxy-5-methylphenyl)ethyl]-4-methylphenyl acrylate, 2-t-butyl-6-(3-t-butyl-2-hydroxy-5-methylbenzyl)-4-methylphenyl methacrylate, 2-t-butyl-6-[1-(3-t-butyl-2-hydroxy-5-methylphenyl)propyl]-4-methylphenyl acrylate, 2-t-butyl-6-(3-t-butyl-5-ethyl-2-hydroxybenzyl)-4-ethylphenyl acrylate, 2-t-butyl-6-[1-(3-t-butyl-2-hydroxy-5-propylphenyl)ethyl]-4-propylphenyl acrylate, 2-t-butyl-6-[1-(3-t-butyl-2-hydroxy-5-isopropylphenyl)ethyl]-4-isopropylphenyl acrylate and the like are exemplified.

Preferable are 2-[1-(2-hydroxy-3,5-di-t-pentylphenyl)ethyl]-4,6-di-t-pentylphenyl acrylate, 2 t-butyl-6-(3-t-butyl-2-hydroxy-5-methylbenzyl)-4-methylphenyl acrylate, 2,4-di-t-butyl-6-[1-(3,5-di-t-butyl-2-hydroxyphenyl)ethyl]phenyl acrylate, 2-t-butyl-6-[1-(3-t-butyl-2-hydroxy-5-methylphenyl)ethyl]-4-methylphenyl acrylate, 2-t-butyl-6-[1-(3-t-butyl-2-hydroxy-5-methylphenyl)propyl]-4-methylphenyl acrylate, 2-t-butyl-6-[1-(3-t-butyl-2-hydroxy-5-propylphenyl)ethyl]-4-propylphenyl acrylate and 2-t-butyl-6-[1-(3-t-butyl-2-hydroxy-5-isopropylphenyl)ethyl]-4-isopropylphenyl acrylate.

More preferable is 2-[1-(2-hydroxy-3,5-di-t-pentylphenyl)ethyl]-4,6-di-t-pentylphenyl acrylate or 2-t-butyl-6-(3-t-butyl-2-hydroxy-5-methylbenzyl)-4-methylphenyl acrylate.

The above-described compound (1) can be produced according to methods described, for example, in JP-A No. 59-144733, JP-A No. 1-168643, JP-A No. 4-264051, U.S. Pat. No. 4,525,514, U.S. Pat. No. 4,562,281 and U.S. Pat. No. 4,365,032 and the like.

The method of producing a granular substance of the present invention contains the following steps.

(i) a step of melting a compound of the formula (1), (ii) a step of dropping the melted substance obtained in the step (i) into water, and recovering a granular substance.

The above-described step (i) is a step of melting a compound (1). Specifically, a compound (1) is melted by heating at a temperature not lower than the melting point Tm° C. of the compound (1). The temperature for heating to melt a compound (1) is not particularly restricted providing it is not lower than Tm° C., and a range of Tm° C. to (Tm+50)° C. is preferable, a range of (Tm+5)° C. to (Tm+40)° C. is more preferable, and a range of (Tm+10)° C. to (Tm+30)° C. is particularly preferable.

The above-described step (ii) is a step of dropping the melted substance obtained in the step (i) into water and solidifying (cooling) this to obtain a granular substance. It is preferable that water to be used in this step (ii) contains a surfactant.

As the surfactant to be used in the present invention, various nonionic surfactants are exemplified such as known propylene glycol fatty acid esters, glycerin fatty acid esters, sorbitan fatty acid esters, polyoxyethylenealkylamines and the like.

Specifically exemplified are propylene glycol monolaurate, propylene glycol monopalmitate, propylene glycol monostearate, propylene glycol monooleate, propylene glycol monobehenate, sorbitan monostearate, sorbitan palmitate, sorbitan tristearate, sorbitan trioleate, sorbitan monooleate, glycerin monostearate, glycerin monopalmitate, glycerin monobehenate, glycerin monodistearate and the like.

The above-described surfactant has an HLB value of preferably 2 to 6, more preferably 3 to 5. When the HLB value is 2 or more, dispersibility of the melted substances dropped into water is excellent, and when 6 or less, mutual adhesion of melted substances is prevented when the melted substances are dropped, and its shape can be maintained when solidified, thus, the above-described range is preferable.

The HLB value of a surfactant in the present invention is one index representing a balance between hydrophilic groups and lipophilic groups of an emulsifier, and is represented by a value between 20 to 0, and the larger the numerical value, the larger the hydrophilicity.

Specifically, its value is determined by the Atlas method and can be obtained according to the following formula, for fatty acid esters.

$$HLB=20\times(1-SV/NV)$$

(wherein, SV represents the saponification value of a fatty acid ester, and NV represents the neutralization value of a constituent fatty acid.)

In the present invention, particularly preferable surfactants include glycerin monostearate (HLB: 2.8 to 3.8) and sorbitan monostearate (HLB: about 4.7).

The concentration of a surfactant in water in the above-described step (ii) is usually 0.1 to 3 wt %, preferably 0.3 to 1 wt %. When 0.1 wt % or more, there is a preferable tendency of preventing mutual adhesion of the resulting granular substances, and when 3 wt % or less, there is a preferable tendency of reduction of load in a drainage treatment.

The temperature of water in the above-described step (ii) is not particularly restricted providing it is lower than the melting point of a compound of the formula (1), and from the standpoint of economy, it is preferably 20° C. or higher, more preferably 20 to 50° C., and further preferably 20 to 45° C.

Though the time for keeping the temperature of water in the above-described step (ii) is not particularly restricted, the temperature is kept (thermally insulated) preferably for 1 minute or longer, more preferably for 2 minutes or longer, directly after attaining the above-described temperature range. From the standpoint of productivity, the solidification time is preferably 24 hours or less.

The method of spraying or dropping the above-described melted compound (1) includes, specifically, a method in which the above-described melted compound (1) is dropped, for example, from a dropping tube; and the like.

In the above-described step (ii), a dropping substance is dropped into water, optionally mixed with a surfactant and is solidified, and the slurry concentration of the granular substance generated in this procedure in the liquid is usually 5 to 40 parts by weight, preferably 10 to 30 parts by weight with respect to 100 parts by weight the whole liquid.

In the above-described step (ii), a dropping substance is usually cooled and solidified in liquid, and in this procedure, it may also be permissible to mix a crystal of a compound (1) or the like as a seed crystal into the liquid to cause solidification.

The melted substance (granular substance) solidified in water in the above-described step (ii) can be recovered usually by a filtration apparatus such as a centrifugal filtration apparatus, Funda filtration apparatus and the like, if necessary after washing with water and the like. The recovered granular substance can also be dried using a drier such as a vacuum drier, ventilation drier, vibration flow drier and the like if necessary.

Thus obtainable granular substance is a granular substance in the form of, for example, disc, approximate sphere, approximate hemisphere and the like. The granular substance in the form of disc, approximate sphere or approximate hemisphere is obtained by dropping the melted substance containing a compound (1). When the grain size is smaller, its shape is usually sphere, and when larger, its shape becomes hemisphere by flattening due to its own weight.

When the granular substance is spherical, its grain size is usually 1 mm to 5 mm, and when approximate hemisphere, its grain size is 1 mm to 4 mm and its height is 1 mm to 4 mm. From the standpoint of dispersibility into a thermoplastic polymer, its grain size is preferably 1 mm to 4 mm in the case of sphere, and its grain size is preferably 2 mm to 4 mm and its height is preferably 1 mm to 3 mm in the case of approximate hemisphere.

With respect to the granular substance obtained by the production method of the present invention, the weight per grain of the granular substance is usually 5 mg to 100 mg, preferably 6 mg to 50 mg. Within this range, there is a preferable tendency that dusting is suppressed and mutual adhesion of the granular substances is suppressed.

With respect to the weight of the granular substance, the amount of dropping of the melted substance may be advantageously controlled by the size of a pore, the viscosity of the melted substance and the like in the case of performing dropping in the solidification step and in the case of use of a dropping tube.

The granular substance obtained by the production method of the present invention is a crystalline granular substance. Namely, the granular substance obtained by the production method of the present invention shows usually an endothermic peak in 110 to 130° C. when temperature is raised at a rate of 10° C./min in a differential scanning calorimeter (DSC).

The granular substance obtained by the production method of the present invention contains a compound (1), and can be suitably used as a stabilizer for polymers such as thermoplastic polymers and the like. The granular substance contains a compound (1) in an amount of usually 95 wt % or more, preferably 99 wt % or more.

The granular substance can contain a material which is capable of showing an endothermic peak in 110 to 130° C., and for example, a phenolic antioxidant or the like may be contained.

The granular substance obtained by the production method of the present invention causes little dusting and its handling is easy, and is excellent in what is called blocking resistance by which blocking (cohesion) does not occur even in storage for a long period of time since it is crystallized. Further, when the granular substance obtained by the production method of the present invention is blended in melt-kneading in a thermoplastic polymer such as polypropylene and the like, it shows the same excellent dispersibility as that of conventional powdery granular substances, even if the granular substance is used in the form of grain intact.

Here, examples of the thermoplastic polymer include polypropylene type resins such as an ethylene-propylene copolymer and the like; polyethylene type resins (high density polyethylene (HD-PE), low density polyethylene (LD-PE), linear low density polyethylene (LLDPE) and the like); methylpentene polymer, ethylene-ethyl acrylate copolymer, ethylene-vinyl acetate copolymer; polystyrenes (polystyrene such as poly(p-methylstyrene), poly(α-methylstyrene) and the like, acrylonitrile-styrene copolymer, acrylonitrile-butadiene-styrene copolymer, special acrylic rubber-acrylonitrile-styrene copolymer, acrylonitrile-chlorinated polyethylene-styrene copolymer, styrene-butadiene copolymer, and the like), chlorinated polyethylene, polychloroprene, chlorinated rubber, polyvinyl chloride, polyvinylidene chloride, methacrylic resin, ethylene-vinyl alcohol copolymer, fluorine resin, polyacetal, grafted polyphenylene ether resin, polyphenylene sulfide resin, polyurethane, polyamide, polyester resins (for example, polyethylene terephthalate, polybutylene terephthalate and the like), polycarbonate, polyacrylate, polysulfone, polyether ether ketone, polyether sulfone, aromatic polyester resin, diallyl phthalate prepolymer, silicone resin, 1,2-polybutadiene, polyisoprene, butadiene/acrylonitrile copolymer, ethylene-methyl methacrylate copolymer, and the like, and particularly from the standpoint of good molding processability, preferable are polyethylene type resins, polypropylene type resins and polystyrenes, and more preferable are polypropylene type resins, acrylonitrile-butadiene-styrene copolymer and styrene-butadiene copolymer.

Here, the polypropylene type resin means a polyolefin containing a structural unit derived from propylene, and specifically mentioned are a crystalline propylene homopolymer, propylene-ethylene random copolymer, propylene-α-olefin random copolymer, propylene-ethylene-α-olefin copolymer, polypropylene type block copolymers composed of a propylene homopolymer component or copolymer component mainly composed of propylene, the content of propylene in the copolymer component mainly composed of propylene is usually more than 80 wt %, and of a copolymer component of propylene and ethylene and/or α-olefin; and the like.

In the present invention, when the polypropylene type resin is used as the thermoplastic polymer, polypropylene type resins may be used singly or two or more of them may be blended and used.

The α-olefin is usually an α-olefin having 4 to 12 carbon atoms, and examples thereof include 1-butene, 1-pentene, 1-hexene, 4-methyl-1-pentene, 1-octene, 1-decene and the like, and preferable are 1-butene, 1-hexene and 1-octene.

Examples of the propylene-α-olefin random copolymer include a propylene-1-butene random copolymer, propylene-1-hexene random copolymer, propylene-1-octene random copolymer, and the like.

Examples of the propylene-ethylene-α-olefin copolymer include a propylene-ethylene-1-butene copolymer, propylene-ethylene-1-hexene copolymer, propylene-ethylene-1-octene copolymer and the like.

In the polypropylene type block copolymer composed of a propylene homopolymer component or copolymer component mainly composed of propylene, and of a copolymer component of propylene and ethylene and/or α-olefin, examples of the copolymer component mainly composed of propylene include a propylene-ethylene copolymer component, propylene-1-butene copolymer component, propylene-1-hexene copolymer component and the like, and examples of the copolymer component of propylene and ethylene and/or α-olefin include a propylene-ethylene copolymer component, propylene-ethylene-1-butene copolymer component, propylene-ethylene-1-hexene copolymer component, propylene-ethylene-1-octene copolymer component, propylene-1-butene copolymer component, propylene-1-hexene copolymer component, propylene-1-octene copolymer component and the like. The content of ethylene and/or α-olefin having 4 to 12 carbon atoms in the copolymer component of propylene and ethylene and/or α-olefin is usually 0.01 to 20 wt %.

Examples of the polypropylene type block copolymer composed of a propylene homopolymer component or copolymer component mainly composed of propylene, and of a copolymer component of propylene and ethylene and/or α-olefin include a propylene-ethylene block copolymer, (propylene)-(propylene-ethylene) block copolymer, (propylene)-(propylene-ethylene-1-butene) block copolymer, (propylene)-(propylene-ethylene-1-hexene) block copolymer, (propylene)-(propylene-1-butene) block copolymer, (propylene)-(propylene-1-hexene) block copolymer, (propylene-ethylene)-(propylene-ethylene-1-butene) block copolymer, (propylene-ethylene)-(propylene-ethylene-1-hexene) block copolymer, (propylene-ethylene)-(propylene-1-butene) block copolymer, (propylene-ethylene)-(propylene-1-hexene) block copolymer, (propylene-1-butene)-(propylene-ethylene) block copolymer, (propylene-1-butene)-(propylene-ethylene-1-butene) block copolymer, (propylene-1-butene)-(propylene-ethylene-1-hexene) block copolymer, (propylene-1-butene)-(propylene-1-butene) block copolymer, (propylene-1-butene)-(propylene-1-hexene) block copolymer and the like.

When the polypropylene type resin is used as the thermoplastic polymer in the present invention, preferable are polypropylene type block copolymers composed of a crystalline propylene homopolymer, propylene homopolymer component or copolymer component mainly composed of propylene, and of a copolymer component of propylene and ethylene and/or α-olefin having 4 to 12 carbon atoms, and more preferable are polypropylene type block copolymers composed of a propylene homopolymer component or copolymer component mainly composed of propylene, and of a copolymer component of propylene and ethylene and/or α-olefin having 4 to 12 carbon atoms.

The granular substance obtained by the production method of the present invention may be blended, as a granular polymer stabilizer, in an amount of usually 2 parts by weight or less, specifically, 0.01 part by weight or more and 2 parts by weight or less, preferably 0.01 part by weight or more and 1 part by weight or less, with respect to 100 parts by weight of a thermoplastic polymer. When the amount is 2 parts by weight or less, there is a preferable tendency of suppressing a so-called bleed phenomenon in which a stabilizer emerges on the surface of a thermoplastic polymer composition.

EXAMPLES

The present invention will be illustrated further in detail by examples and comparative examples mentioned below, but the present invention is not limited to them.

In the following examples and comparative examples, 2-[1-(2-hydroxy-3,5-di-t-pentylphenyl)ethyl]-4,6-di-t-pentylphenyl acrylate (hereinafter, referred to as compound (1-1). melting point>115° C.) was used as the compound (1). The properties of the granular substance were measured and evaluated as described below.

[Grain Size Distribution Measuring Method]

The grain size distribution was measured using an automated sonic sieving particle size analyzer robot sifter RPS-105 manufactured by Seishin Enterprise Co., Ltd. Those of 74 µm or less (in Table 1, 75 µm Pass) are recognized as a fine powder, and the smaller this numerical value is, then, smaller the dusting and lower the crisis of dust explosion.

[Weight Measuring Method]

The weight of one grain of the resultant granular substance was measured using a precision balance manufactured by METTLER TOLEDO. The same measurement was repeated 20 times for each sample, and its average value was used as the weight of each one grain of the granular substance.

[Differential Scanning Calorimetry]

The granular substance was heated up at a rate of 10° C./min and endothermic peaks thereof (° C.) were measured, by a differential scanning calorimeter (DSC) DSC-60A manufactured by Shimadzu Corp.

Comparative Example 1

Into a four-necked flask equipped with a thermometer, stirring machine and cooling tube was charged 494.8 g (1.0 mol) of 2,2'-ethylidenebis(4,6-di-t-pentylphenol), 72.1 g (1.0 mol) of acrylic acid, 400 g of n-heptane and 212.5 g (2.1 mol) of triethylamine, and an atmosphere in the vessel was purged with nitrogen, then, 107.3 g (0.7 mol) of phosphorus oxychloride was dropped while stirring. After completion of dropping, the temperature was insulated at 80° C. for 1 hour, then, 500 g of water was charged, and the mixture was washed with water at 60° C. and liquid separation was caused. Water-washing and liquid separation of the oil layer portion were repeated until neutralization, and the oil layer was cooled down to 5° C. while stirring, to cause deposition of a crystal. At the same temperature, stirring was further performed, to cause deposition of a crystal, then, the crystal was filtrated, and washed with cold n-heptane, and dried under reduced pressure to obtain 235.6 g of a compound (1-1) in the form of crystalline powder. The resultant powder was compacted and pulverized under a compacting pressure of 7.3 MPa by a roller compactor manufactured by Turbo Kogyo Co., Ltd, to obtain a granulated material. The resultant granulated material showed an endothermic peak at 120.5° C. The weight of one grain of this granulated material was 1.2 mg/grain. The results of grain size distribution are shown in Table 1. This powder manifested significant dusting.

Example 1

The powdery compound (1-1) obtained in Comparative Example 1 was heated up to 140° C. and stirred in a vessel to cause melting thereof, then, the melted substance of the compound (1-1) was dropped into mixed liquid composed of 100 parts by weight of water adjusted to 45° C. and 0.5 parts by weight of glycerin monostearate (Electro-Stripper TS-5 manufactured by Kao Corp.; HLB value 3.8), and stirred in the liquid for 15 hours. Thereafter, the mixture was washed with water and filtrated using a funnel, then, dried at 80° C. using a gear oven, to obtain 35 parts by weight of a compound (1-1) in the form of approximate sphere. The resultant granular substance showed an endothermic peak at 121.2° C. The weight of one grain of this granular substance was 24.3 mg/grain. The results of measurement of grain size distribution of the granular substance are shown in Table 1. This granular substance manifested utterly no dusting, and handling thereof was easy.

TABLE 1

|   | Comparative Example 1 | Example 1 |
|---|---|---|
| 2000 µm ON | 0.00% | 99.65% |
| 1000 µm ON | 33.20% | 0.26% |
| 500 µm ON | 42.21% | 0.09% |
| 300 µm ON | 15.32% | 0.00% |
| 150 µm ON | 5.40% | 0.00% |
| 106 µm ON | 1.29% | 0.00% |
| 75 µm ON | 1.29% | 0.00% |
| 75 µm PASS | 1.29% | 0.00% |

Example 2

Fifteen parts by weight of a compound (1-1) in the form of approximate sphere was obtained in the same manner as in Example 1, excepting that the powdery compound (1-1) obtained in Comparative Example 1 was heated up to 140° C. and stirred in a vessel to cause melting thereof, then, the melted substance of the compound (1-1) was dropped into mixed liquid composed of 100 parts by weight of water adjusted to 45° C. and 0.5 parts by weight of sorbitan monostearate (SPAN60 manufactured by Wako Pure Chemical Industries, Ltd.; HLB value 4.7), in Example 1. The resultant granular substance showed an endothermic peak at about 121° C. The weight of one grain of this granular substance was 20.4 mg/grain. The resultant granular substance manifested utterly no dusting and handling thereof was easy, like in Example 1.

INDUSTRIAL APPLICABILITY

The granular substance obtained by the production method of the present invention shows little dusting and handling thereof is easy, thus, this granular substance can be suitably used for improving the processing stability of a polymer such as polybutadiene and the like.

The invention claimed is:

1. A method of producing a granular substance comprising
(i) a step of melting a compound of the formula (1):

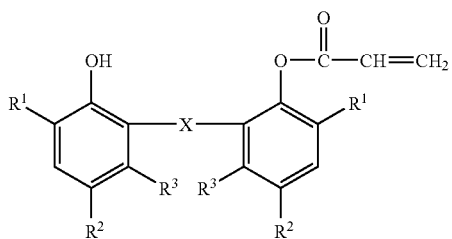

(1)

(wherein, $R^1$ and $R^2$ represent each independently a hydrogen atom, alkyl group having 1 to 8 carbon atoms or cycloalkyl group having 5 to 8 carbon atoms, $R^3$ represents a hydrogen atom or alkyl group having 1 to 8 carbon atoms, X represents a single bond, sulfur atom, oxygen atom, alkylidene group having 1 to 8 carbon atoms or cycloalkylidene group having 5 to 8 carbon atoms) to obtain the melted substance, and (ii) a step of dropping the melted substance obtained in the step (i) into water containing a surfactant having an HLB value of 2 to 6 and recovering the granular substance.

2. The production method according to claim 1, wherein the melted substance obtained in the step (i) is dropped into water having a temperature which is not lower than 20° C. and lower than the melting point of the compound of the formula (1).

3. The production method according to claim 1, wherein the weight or per grain of the resultant granular substance is 5 mg to 100 mg.

4. The production method according to claim 1, wherein the compound of the formula (1) is 2-[1-(2-hydroxy-3,5-di-t-pentylphenyl)ethyl]-4,6-di-t-pentylphenyl acrylate or 2-t-butyl-6-(3-t-butyl-2-hydroxy-5-methylbenzyl)-4-methylphenyl acrylate.

5. The production method according to claim 1, wherein the resultant granular substance has a shape of disc, approximate sphere or approximate hemisphere.

\* \* \* \* \*